(12) United States Patent
Thireos et al.

(10) Patent No.: US 6,465,179 B1
(45) Date of Patent: Oct. 15, 2002

(54) DNA ENCODING AN ARTHROPOD CHITIN SYNTHASE

(75) Inventors: George Thireos; Dimitris Kafetzopoulos, both of Heraklion (GR)

(73) Assignee: Foundation for Research and Technology-Hellas, Heraklion/Crete (GR)

( * ) Notice: Subject to any disclaimer, the term of this patent is extended or adjusted under 35 U.S.C. 154(b) by 0 days.

(21) Appl. No.: 09/230,041
(22) PCT Filed: May 20, 1998
(86) PCT No.: PCT/EP98/02970
§ 371 (c)(1),
(2), (4) Date: Jan. 19, 1999
(87) PCT Pub. No.: WO98/53053
PCT Pub. Date: Nov. 26, 1998

(30) Foreign Application Priority Data

May 21, 1997 (EP) ............................................ 97108240

(51) Int. Cl.[7] .............................. C12Q 1/68; C12N 9/10
(52) U.S. Cl. ......................... 435/6; 435/69.1; 435/193; 435/320.1; 435/69.2; 435/252.3; 536/23.2
(58) Field of Search ................................ 435/193, 69.1, 435/69.2, 320.1, 6, 252.3; 536/23.2

(56) References Cited

U.S. PATENT DOCUMENTS 5,824,545 A * 10/1998 Koltin et al. ............ 435/320.1

* cited by examiner

Primary Examiner—Rebecca E. Prouty
Assistant Examiner—Richard Hutson
(74) Attorney, Agent, or Firm—McDermott, Will & Emery

(57) ABSTRACT

The present invention relates to nucleic acids comprising a nucleotide sequence encoding at least a portion of an enzyme which catalyzes the synthesis of chitin in arthropods, inhibitors directed to said enzyme, and a method for developing said inhibitors.

7 Claims, 5 Drawing Sheets

FIGURE 1

```
GCC ATT GGA CAC TGG CTG CAA AAG GCG ACG
 A   I   G   H   W   L   Q   K   A   T

GAG CAT GTC ATT GGT TGC GTC CTC TGC AGT
 E   H   V   I   G   C   V   L   C   S

CCG GGA TGC TTC AGT CTG TTC CGG GCC ACC
 P   G   C   F   S   L   F   R   A   T

GCC CTG ATG GAG AAC AGC GTG ATG AAG CGG
 A   L   M   E   N   S   V   M   K   R

TAC ACG ATG ATC AGT TCG GAG GCG ATG AAG
 Y   T   M   I   S   S   E   A   M   K

ATG GTG CAG TAC GAC CAG GGC GAG GAC CGC
 M   V   Q   Y   D   Q   G   E   D   R

TGG CTG TGT ACG CTG CTC TTG AAG GCC GGC
 W   L   C   T   L   L   L   K   A   G

TTC CGG GTG GAG TAC TGG GGC GCC TTG GAT
 F   R   V   E   Y   W   G   A   L   D

GGG TAT ACC CAA GCG CCA GAG AGC TTT AAC
 G   Y   T   Q   A   P   E   S   F   N

GAG TTC TAC AAC CAA CGA AGT CGT TGG ATC
 E   F   Y   N   Q   R   S   R   W   I
```

FIGURE 2

```
GCC ATT GGA CAC TGG CTG CAA AAG GCG ACG
 A   I   G   H   W   L   Q   K   A   T

GAG CAT GTC ATT GGT TGC GTC CTC TGC AGT
 E   H   V   I   G   C   V   L   C   S

CCG GGA TGC TTC AGT CTG TTC CGG GCC ACC
 P   G   C   F   S   L   F   R   A   T

GCC CTG ATG GAG AAC AGC GTG ATG AAG CGG
 A   L   M   E   N   S   V   M   K   R

TAC ACG ATG ATC AGT TCG GAG GCG ATG AAG
 Y   T   M   I   S   S   E   A   M   K

ATG GTG CAG TAC GAC CAG GGC GAG GAC CGC
 M   V   Q   Y   D   Q   G   E   D   R

TGG CTG TGT ACG CTG CTC TTG AAG GCC GGC
 W   L   C   T   L   L   L   K   A   G

TTC CGG GTG GAG TAC TGC GGC GCC TCG GAT
 F   R   V   E   Y   C   G   A   S   D

GGG TAT ACC CAC GCG CCA GAG AGC TTT AAC
 G   Y   T   H   A   P   E   S   F   N

GAG TTC TAC AAC CAA CGA CGC CGT TGG ATC
 E   F   Y   N   Q   R   R   R   W   I
```

Figure 3

```
GCC CTC ATG GAT GAC AAT GTG ATG AAG AAA
 A   L   M   D   D   N   V   M   K   K

TAC ACG ACA CGG TCG GAT GAG GCT CGT CAC
 Y   T   T   R   S   D   E   A   R   H

TAC GTG CAG TAC GAT CAG GGC GAG GAT CGT
 Y   V   Q   Y   D   Q   G   E   D   R

TGG CTG TGC ACA TTG CTC CTC CAG AGG GGA
 W   L   C   T   L   L   L   Q   R   G

TAC CGC GTG GAG TAC TCG GCT GCC AGT GAT
 Y   R   V   E   Y   S   A   A   S   D

GCG TAC ACC CAC GCC CCC GAG GGA TTC AAT
 A   Y   T   H   A   P   E   G   F   N

GAG TTC TAC AAC CAG CGG CGG AGA TGG GTG
 E   F   Y   N   Q   R   R   R   W   V
```

FIGURE 4

```
                      .   . .  *.    *  . .*
        Dmechs     AIGHWLQKATEHVIGCVLCSPGCFSLFR...........
        Celchs     AIAHWFQKAAEHVFGCVLCAPGCFSLFR.\.........
        Scechs1    KMSNILDKTTESNFGFITVLPGAFSAYRFEAVRGQ....
        Scechs2    KISNILDKPLESVFGYISVLPGALSAYRYRALKNHEDGT
        Scechs3    YISHHQAKAFESVFGSVTCLPGCFSMYRIKSPKGSDGYW
        Rlenodc    WLACNEERAAQARFGAVMCCCGPCAMYR...........

*                      *** *
        Dmechs     ATALMENSVMKRYTMISSEAMKMVQ.YD....QGEDRWLC
        Celchs     ASALMDDNIMHKYTKTASEPRHYVQ.YD....QGEDRWLS
        Scechs1    .P......LQKYFYGEIMENEGFHFFSSNMYLAEDRILC
        Scechs2    GP......LRSYFLGETQEGRDHDVFTANMYLAEDRILC
        Scechs3    VPVLANPDIVERYSDNVTNTLHKKNLLL....LGEDRFLS
        Rlenodc    RSAML..SLLDQY...ETQLYRGKP.SD....FGEDRHLT .         . * *.      *  **
        Dmechs     .TLLLK..AGFRVEYWGALDGYTQAPESFNEFYNQRSRWI
        Celchs     .TLLLK..QGYRIEYAAASDAETYAPEGFEEFFNQRRRWT
        Scechs1    FEVVTKKNCNWILKYCRSSYASTDVPERVPEFILQRRRWL
        Scechs2    WELVAKRDAKWVLKYVKEATGETDVPEDVSEFISQRRRWL
        Scechs3    .SLMLKTFPKRKQVFVPKAACKTIAPDKFKVLLSQRRRWI
        Rlenodc    .ILMLS..AGFRTEYVPSAIAATVVPDTMGVYLRQQLRWA
```

```
                            *                            *** *
    Dmechs2    ALMDDNVMKKYTTRSDEARHYVQ.YD....QGEDRWLC.
     Celchs    ALMDDNIMHKYTKTASEPRHYVQ.YD....QGEDRWLS.
    Scechs1    .......LQKYFYGEIMENEGFHFFSSNMYLAEDRILCF
    Scechs2    .......LRSYFLGETQEGRDHDVFTANMYLAEDRILCW
    Scechs3    VLANPDIVERYSDNVTNTLHKKNLLL...LGEDRFLS.
    Rlenodc    AML   SLLDQY    ETQLYRGKP SD     FGEDRHLT.

.         .       * *.        *   **
    Dmechs2    TLLLQ..RGYRVEYSAASDAYTHAPEGFNEFYNQRRRWV
     Celchs    TLLLK..QGYRIEYAAASDAETYAPEGFEEFFNQRRRWT
    Scechs1    EVVTKKNCNWILKYCRSSYASTDVPERVPEFILQRRRWL
    Scechs2    ELVAKRDAKWVLKYVKEATGETDVPEDVSEFISQRRRWL
    Scechs3    SLMLKTFPKRKQVFVPKAACKTIAPDKFKVLLSQRRRWI
    Rlenodc    ILMLS   AGFRTEYVPSAIAATVVPDTMGVYLRQQLRWA
```

FIGURE 5

DNA ENCODING AN ARTHROPOD CHITIN SYNTHASE

The present invention relates to nucleic acids comprising a nucleotide sequence encoding at least a portion of an enzyme which catalyzes the synthesis of chitin in arthropods, inhibitors directed to said enzyme, and a method for developing said inhibitors.

Chitin is a carbohydrate homopolymer of β(1→4) linked N-acetylglucosamine. Chitin is a structural polysaccharide occurring mainly in the cell wall of some fungi and in exoskeleton of the arthropods.

Chitin is synthesized by the action of specialized enzymes, referred to as chitin synthases, that catalyze the polymerization of N-acetylglucosaminyl residues into chitin from uridine 5'-diphospho-N-acetylglucosamine.

Chitin synthases belong to a group of enzymes that catalyze the synthesis of linear structural polysaccharides and are collectively termed as processive glycosyltransferases. The primary structures of the known processive glycosyl transferases (i.e. the fungal chitin synthases, the prokaryotic and eukaryotic cellulose synthases, the prokaryotic and eukaryotic hyaluronan synthases, the prokaryotic alginate synthases and the rhizobial chito-oligosaccharide synthases) present some sequence similarities suggesting that these UDP-sugar utilizing enzymes show a similar mode of action. Despite the similarities, the various processive glucosyltransferases display substantial differences mainly in their substrate specificities, their activation and inhibition parameters, the size and conformation of their products.

Since several arthropod species are considered as plant and animal pests, the inhibition of the chitin synthesis machinery has been viewed in particular as an attractive target for the development of pest control agent.

Known insect chitin synthesis inhibitors, either natural or synthetic, fall within two main categories: (a) direct inhibitors of chitin synthesis such as the Streptomyces antibiotics Nikkomycins and Polyoxins and (b) insect growth regulators that interfere indirectly but drastically with the synthesis of chitin in insects, such us the benzoylphenyl-urea derivatives.

Although the studies for the identification of these compounds have a history of several decades, the action of chitin synthesis inhibitors is still inadequately understood. This is due to both the limited availability of suitable insect chitin synthase enzyme preparations and to the lack of any molecular insight on the chitin synthesis and its regulation in insects.

Thus, the technical problem underlying the present invention is to provide new inhibitors for the chitin synthesis in order to prevent damages caused by arthropods.

The solution to the above technical problem is achieved by providing the embodiments characterized in the claims.

In particular, there is provided a nucleic acid which comprises a nucleotide sequence encoding at least a portion of an enzyme which catalyzes the synthesis of chitin in arthropods.

The terms "nucleic acid" and "nucleotide sequence" refer to endogenously expressed, semisynthetic, synthetic or chemically modified acid molecules of deoxyribonucleotides and/or ribonucleotides. In a preferred embodiment of the present invention the nucleotide sequence include sequences as illustrated in FIGS. 1 3 (SEQ ID NO:1), allelic derivatives of said sequences and DNA-sequences degenerated as a result of the genetic code for said sequences. It also includes DNA sequences hybridizing under stringent conditions with the nucleotide sequence defined above.

Although said allelic, degenerate and hybridising sequences may have structural divergences due to (naturally occurring) mutations, such as small deletions or substitutions, they will usually still exhibit essentially the same useful properties, allowing their use in basically the same applications.

In a preferred embodiment the present invention relates to an isolated DNA sequence encoding a portion of an enzyme which catalyzes the synthesis of chitin in arthropods. Specific embodiments include DNA sequences which are characterized by the ability to hybridize to the DNA sequence represented in FIG. 1 at e.g. 55° C. or encode a polypeptide reactive with an antibody against the polypeptide containing the deduced amino acid sequence in FIGS. 1 to 3. The invention also relates to a DNA expression construct containing the isolated DNA sequences and encoding an enzyme having the specificity described above.

The present invention also relates to recombinant molecules comprising the nucleic acid as described above optionally linked to an expression-control sequence. Such vectors may be useful in the production of at least said portion of an enzyme in stable or transiently transformed cells. Several animal, plant, fungal and bacterial systems may be used for the transformation and subsequent cultivation process. Preferably, expression vectors which can be used in the invention contain sequences necessary for the replication in the host cell and are autonomously replicable. It is also preferable to use vectors containing selectable marker genes which can be easily selected for transformed cells. The necessary preparation is well known to those skilled in the art.

It is another object of the invention to provide a host cell transformed by an expression plasmid of the invention and capable of producing at least said portion of an enzyme. Examples of suitable host cells include various eukaryotic and prokaryotic cells, such as *E. coli,* insect cells, plant cells, mammalian cells, and fungi such as yeast.

Another object of the present invention is to provide a polypeptide comprising at least a portion of an enzyme which catalyzes the synthesis of chitin in arthropods. The term "polypeptide" includes the complete enzyme or a biologically active or inactive fragment thereof encoded by the sequences described above and displaying preferably biologically features of said enzyme. The amino acid sequences of specially preferred polypeptides contain the sequences displayed in FIGS. 1 3 (SEQ ID NO:2).

It is a further aspect of the invention to provide a process for the production of the above mentioned polypeptide. Such a process comprises cultivating a host cell being transformed with a nucleic acid sequence of the present invention in a suitable culture medium and purifying the produced polypeptide. Thus, this process allows the production of the sufficient amount of the desired polypeptide for use in applications described herein below. The host cell is obtainable from bacteria such as *E. coli,* from fungi, such as yeast, from plants such as tobacco, potato, or Arabidopsis, and from animals, in particular vertebrate cells such as the CHO-cells.

The invention also relates to the methods for assaying the effects of various compounds on the expression and the biological activity of arthropod chitin synthases. In these methods the polypeptide in enzymatically active form, preferably the enzyme chitin synthase of an arthropod is produced by recombinant DNA techniques in which an isolated DNA sequence encoding the enzyme is expressed from a DNA expression construct as outlined above.

The figures show:

FIGS. 1 to 3 show DNA sequence (SEQ ID NO:1) and the deduced amino acid sequence (SEQ ID NO:2) of a portion of chitin synthase of *Drosophila melanogaster.*

FIGS. 4 and 5 show multiple protein sequence alignments of the portion of chitin synthase of *Drosophila melanogaster* with the corresponding regions of a nematode, three yeast chitin syntheses and a rhizobial chito-oligosaccharide synthase. In particular, the multiple sequence alignments show the isolated portion of *Drosophila melanogaster* chitin synthase (Dmechs1 in FIG. 4, and Dmechs2 in FIG. 5) with the corresponding regions of the nematode chitin synthase (Celchs), the chitin synthase 1 (Scechs1), the chitin synthase 2 (Scechs2) and chitin synthase 3 (Scechs3) of yeast and the rhizobial chito-oligosaccharide synthase (RlenodC). The dots above the alignment indicate similarity and the asterisks identity.

In the following preferred embodiments of the present invention are outlined in more detail.

With the isolation of the first insect chitin synthase disclosed here, that of *Drosophila melanogaster* (fruitfly), recombinant methodology for the expression, purification and identification of chitin synthases can be used. These methods employed in assays for the evaluation and characterization of insect chitin synthase inhibitors can lead to the development of new potent pest control agents.

The present invention was made possible with identification of the DNA sequence shown in FIGS. 1 to 3, encoding for a portion of chitin synthase of *Drosophila melanogaster*.

A search of the GENBANK databank using the deduced amino acid sequence of *Drosophila melanogaster* sequence revealed significant similarities with a nematode sequence presumably encoding for a chitin synthase, with several sequences encoding for fungal chitin syntheses, and with several rhizobial chito-oligosaccharide syntheses. The multiple sequence alignments of the *Drosophila melanogaster* chitin synthase with these sequences are presented in FIGS. 4 and 5.

Despite the sequence similarities of the *Drosophila melanogaster* chitin synthase with above described enzymes, hybridization of the *Drosophila melanogaster* DNA to neither the nematode nor the fungal genomic DNA could be observed even at low stringency conditions (0.75M [$Na^+$], 55° C.).

With the isolation of the new insect chitin synthase gene, that of *D. melanogaster*, the use of recombinant methodology in the production, characterization and identification of arthropod chitin synthases can be employed.

By reference to the DNA sequence listed below, hybridization, immunochemical or polymerase chain reaction amplification methods can be used for the isolation of either cDNA or genomic DNA of chitin synthase from this species. The same approaches can be used for the identification and isolation of DNA encoding the chitin synthases of other arthropod species.

The isolated DNA sequences which fall within the scope of this invention can be used to express the encoded chitin synthases in large quantities in either prokaryotic or eukaryotic host cell.

In another aspect, the invention relates to methods for developing pest control agents. Chitin synthases of arthropods can be produced by recombinant DNA methodology as outlined above and used in enzyme assays for the evaluation and characterization of specific chitin synthase inhibitors. These preparations can also be used in the screening for the identification of new chitin synthesis inhibitors.

Further, DNA constructs of the arthropod chitin synthases fused with reporter genes (lacZ, GFP, luciferase) can be used to obtain trangenic insects or tranformed cell lines as outlined above. These animals and cell lines can be used in the evaluation of effect insect growth regulators have in the biosynthesis of chitin.

The present invention will be further illustrated by the following examples.

EXAMPLE 1

A DNA fragment containing the isolated DNA sequence and encoding for the insect chitin synthase is inserted in an expression vector containing a lac inducible promoter. The construct is used to transform *E. coli* cells. Cells are grown in LB medium at half-log phase and the expression of chitin synthase is induced by the addition of 1 mM IPTG.

After 4 hours the cell are harvested by centrifugation and lysed by sonication. The homogenate is centrifuged at 2000 g for 30 minutes at 4° C. and the supernatant of the centrifugation is ultracentrifuged at 100 000 g for one hour. The pellet containing the membrane fraction were resuspended in a buffer containing 25 mM Tris HCl pH 7.0 and 10 mM Magnesium chloride. This membrane preparation is subsequently used in chitin synthase inhibition assays.

The assays are performed by incubating a sample of the membrane fraction with UDP-GlcNAc 5 mM and the compounds tested for chitin synthesis inhibition. The activity of chitin synthase is evaluated by either the measurement of incorporation of radiolabelled GlcNAc from UDP-GlcNAc into chitin or by the spectrophotometric estimation of released UDP by the method of the coupled enzyme reactions assay. Comparison of the measured activity to that obtained under control conditions (no compound added) is used for the evaluation of compounds as a chitin synthase inhibitor.

EXAMPLE 2

A DNA fragment encoding the promoter and a portion of the coding regions of the insect chitin synthase is fused to lacZ reporter gene. The DNA construct containing the translational fusion of Chitin synthase-lacZ is used for the transformation of Kc insect cells. After the selection and isolation of stable tranformants the transformed cell line is used for the testing or screening for compound that affect the transcriptional activation of the chitin synthase gene. In these assays the cell line is incubated with the compounds for 24 hours and the effect of the compounds is evaluated by measuring and comparing the beta-galactosidase activity to that of the control.

EXAMPLE 3

100 ng of the DNA fragment, encoding the sequence presented in FIGS. 1–3 is used for the incorporation of radioactive nucleotides into the double-stranded DNA according the standard "nick translation" methodology. Radioactive DNA probes generated by this method are used for the identification and isolation of clones encoding for chitin syntheses from a genomic DNA cosmid library of *D. melanogaster*. The DNA of the recombinant cosmids is placed (blotted) on nitrocellulose filters, denatured and thin hybridized with the radioactive DNA probe. Hybridisation is performed at low stringency conditions (0.75M [$Na^+$], 55° C.). Filters are then washed and exposed for autoradiography.

Cosmids which hybridized with the probe (positive clones), are isolated and further characterized with restriction enzyme analysis and DNA sequence analysis.

From the procedure described above a second gene (Dmechs2) encoding for chitin synthase in this species is identified and partially sequences. The DNA sequence and the deduced amino acid sequence are presented in FIGS. 1–3.

FIG. 5 shows multiple protein sequence alignment of the portion of Dmechs2 with the corresponding regions of a nematode, three yeast chitin syntheses and a rhizobial chito-oligosaccharide synthase.

What is claimed is:

1. An isolated nucleic acid which comprises a nucleotide sequence that hybridizes under 0.75 M Na$^+$ and 55° C. conditions to the DNA sequence shown in SEQ ID NO:1, wherein said nucleic acid encodes an enzyme which catalyzes the synthesis of chitin in arthropods.

2. The nucleic acid according to claim 1, wherein the nucleotide sequence contains the DNA sequence as shown in SEQ ID NO:1.

3. A recombinant vector comprising a nucleic acid according to claim 2.

4. The recombinant vector according to claim 3, wherein said nucleic acid sequence is functionally linked to an expression-control sequence.

5. A host containing the nucleic acid according to claim 2.

6. A method for developing chitin synthase inhibitors, comprising the steps of:

(a) expressing the nucleic acid of claim 1 in a host cell, and (b) comparing chitinsynthase activity in the presence and absence of test compounds.

7. A host containing the recombinant vector according to claim 3.

* * * * *

UNITED STATES PATENT AND TRADEMARK OFFICE
CERTIFICATE OF CORRECTION

PATENT NO. : 6,465,179 B1
DATED : October 15, 2002
INVENTOR(S) : Thireos et al.

It is certified that error appears in the above-identified patent and that said Letters Patent is hereby corrected as shown below:

Column 1,
Line 63, please replace "FIGS. 1 3 (SEQ ID NO: 1)" with -- FIGS. 1 (SEQ ID NO: 1), 2 (SEQ ID NO: 3), and 3 (SEQ ID NO: 5) --

Column 2,
Line 43, please replace "FIGS. 1 3 (SEQ ID NO: 2)" with -- FIGS. 1 (SEQ ID NO: 2), 2 (SEQ ID NO: 4), and 3 (SEQ ID NO: 6) --
Lines 65-66, please replace "FIGS. 1 to 3 show DNA sequence (SEQ ID NO: 1) and the deduced amino acid sequence (SEQ ID NO: 2)" with -- FIGS. 1 to 3 show DNA sequence (SEQ ID NOs: 1, 3 and 5) and the deduced amino acid sequences (SEQ ID NOs: 2, 4 and 6), respectively, --

Column 4,
Line 48, please replace "FIGS. 1 3" with -- FIG. 2 (SEQ ID NO: 4) --
Line 67, please replace "FIGS. 1 3" with -- FIG. 3 (SEQ ID NOs: 5 and 6) --

Column 23,
Line 16, please replace "shown in SEQ ID NO: 1" with -- selected from the group consisting of SEQ ID NOs: 1, 3 and 5 --

Signed and Sealed this

Twenty-third Day of November, 2004

JON W. DUDAS
*Director of the United States Patent and Trademark Office*

UNITED STATES PATENT AND TRADEMARK OFFICE
CERTIFICATE OF CORRECTION

PATENT NO.   : 6,465,179 B1
DATED        : October 15, 2002
INVENTOR(S)  : George Thireos et al.

It is certified that error appears in the above-identified patent and that said Letters Patent is hereby corrected as shown below:

Column 1,
Line 63, replace "FIGS. 1 (SEQ ID NO: 1), 2 (SEQ ID NO: 3), and 3 (SEQ ID NO: 5)" with -- FIGS. 1 3 (SEQ ID NO: 1) --.

Column 2,
Line 43, replace "FIGS. 1 (SEQ ID NO: 2), 2 (SEQ ID NO: 4), and 3 (SEQ ID NO: 6)" with -- FIGS. 1 3 (SEQ ID NO: 2) --.
Lines 65-66, replace "FIGS. 1 to 3 show DNA sequence (SEQ ID NOs: 1, 3 and 5) and the deduced amino acid sequences (SEQ ID NOs: 2, 4 and 6), respectively," with -- FIGS. 1 to 3 show DNA sequence (SEQ ID NO: 1) and the deduced amino acid sequence (SEQ ID NO: 2) --.

Column 4,
Line 48, replace "FIG. 2 (SEQ ID NO: 4)" with -- FIGS. 1 3 --.
Line 67, replace "FIG. 3 (SEQ ID NOs: 5 and 6)" with -- FIGS. 1 3 --.

Column 23,
Line 16, replace "selected from the group consisting of SEQ ID NOs: 1, 3 and 5" with -- shown in SEQ ID NO: 1 --.

This certificate supersedes Certificate of Correction issued November 23, 2004.

Signed and Sealed this

Thirtieth Day of May, 2006

JON W. DUDAS
*Director of the United States Patent and Trademark Office*

SEQUENCE LISTING

<160> NUMBER OF SEQ ID NOS: 42

<210> SEQ ID NO 1
<211> LENGTH: 810
<212> TYPE: DNA
<213> ORGANISM: Drosophila melanogaster
<220> FEATURE:
<221> NAME/KEY: CDS
<222> LOCATION: (1)..(810)

<400> SEQUENCE: 1

```
gcc att gga cac tgg ctg caa aag gcg acg gag cat gtc att ggt tgc        48
Ala Ile Gly His Trp Leu Gln Lys Ala Thr Glu His Val Ile Gly Cys
 1               5                  10                  15 gtc ctc tgc agt ccg gga tgc ttc agt ctg ttc cgg gcc acc gcc ctg        96
Val Leu Cys Ser Pro Gly Cys Phe Ser Leu Phe Arg Ala Thr Ala Leu
             20                  25                  30 atg gag aac agc gtg atg aag cgg tac acg atg atc agt tcg gag gcg       144
Met Glu Asn Ser Val Met Lys Arg Tyr Thr Met Ile Ser Ser Glu Ala
         35                  40                  45 atg aag atg gtg cag tac gac cag ggc gag gac cgc tgg ctg tgt acg       192
Met Lys Met Val Gln Tyr Asp Gln Gly Glu Asp Arg Trp Leu Cys Thr
     50                  55                  60 ctg ctc ttg aag gcc ggc ttc cgg gtg gag tac tgg ggc gcc ttg gat       240
Leu Leu Leu Lys Ala Gly Phe Arg Val Glu Tyr Trp Gly Ala Leu Asp
 65                  70                  75                  80 ggg tat acc caa gcg cca gag agc ttt aac gag ttc tac aac caa cga       288
Gly Tyr Thr Gln Ala Pro Glu Ser Phe Asn Glu Phe Tyr Asn Gln Arg
                 85                  90                  95 agt cgt tgg atc gcc att gga cac tgg ctg caa aag gcg acg gag cat       336
Ser Arg Trp Ile Ala Ile Gly His Trp Leu Gln Lys Ala Thr Glu His
            100                 105                 110 gtc att ggt tgc gtc ctc tgc agt ccg gga tgc ttc agt ctg ttc cgg       384
Val Ile Gly Cys Val Leu Cys Ser Pro Gly Cys Phe Ser Leu Phe Arg
        115                 120                 125 gcc acc gcc ctg atg gag aac agc gtg atg aag cgg tac acg atg atc       432
Ala Thr Ala Leu Met Glu Asn Ser Val Met Lys Arg Tyr Thr Met Ile
    130                 135                 140 agt tcg gag gcg atg aag atg gtg cag tac gac cag ggc gag gac cgc       480
Ser Ser Glu Ala Met Lys Met Val Gln Tyr Asp Gln Gly Glu Asp Arg
145                 150                 155                 160 tgg ctg tgt acg ctg ctc ttg aag gcc ggc ttc cgg gtg gag tac tgc       528
Trp Leu Cys Thr Leu Leu Leu Lys Ala Gly Phe Arg Val Glu Tyr Cys
                165                 170                 175 ggc gcc tcg gat ggg tat acc cac gcg cca gag agc ttt aac gag ttc       576
Gly Ala Ser Asp Gly Tyr Thr His Ala Pro Glu Ser Phe Asn Glu Phe
            180                 185                 190 tac aac caa cga cgc cgt tgg atc gcc ctc atg gat gac aat gtg atg       624
Tyr Asn Gln Arg Arg Arg Trp Ile Ala Leu Met Asp Asp Asn Val Met
        195                 200                 205 aag aaa tac acg aca cgg tcg gat gag gct cgt cac tac gtg cag tac       672
Lys Lys Tyr Thr Thr Arg Ser Asp Glu Ala Arg His Tyr Val Gln Tyr
    210                 215                 220 gat cag ggc gag gat cgt tgg ctg tgc aca ttg ctc ctc cag agg gga       720
Asp Gln Gly Glu Asp Arg Trp Leu Cys Thr Leu Leu Leu Gln Arg Gly
225                 230                 235                 240
```

```
tac cgc gtg gag tac tcg gct gcc agt gat gcg tac acc cac gcc ccc          768
Tyr Arg Val Glu Tyr Ser Ala Ala Ser Asp Ala Tyr Thr His Ala Pro
            245                 250                 255 gag gga ttc aat gag ttc tac aac cag cgg cgg aga tgg gtg                  810
Glu Gly Phe Asn Glu Phe Tyr Asn Gln Arg Arg Arg Trp Val
        260                 265                 270
```

<210> SEQ ID NO 2
<211> LENGTH: 270
<212> TYPE: PRT
<213> ORGANISM: Drosophila melanogaster

<400> SEQUENCE: 2

```
Ala Ile Gly His Trp Leu Gln Lys Ala Thr Glu His Val Ile Gly Cys
 1               5                  10                  15

Val Leu Cys Ser Pro Gly Cys Phe Ser Leu Phe Arg Ala Thr Ala Leu
             20                  25                  30

Met Glu Asn Ser Val Met Lys Arg Tyr Thr Met Ile Ser Ser Glu Ala
         35                  40                  45

Met Lys Met Val Gln Tyr Asp Gln Gly Glu Asp Arg Trp Leu Cys Thr
     50                  55                  60

Leu Leu Leu Lys Ala Gly Phe Arg Val Glu Tyr Trp Gly Ala Leu Asp
 65                  70                  75                  80

Gly Tyr Thr Gln Ala Pro Glu Ser Phe Asn Glu Phe Tyr Asn Gln Arg
             85                  90                  95

Ser Arg Trp Ile Ala Ile Gly His Trp Leu Gln Lys Ala Thr Glu His
            100                 105                 110

Val Ile Gly Cys Val Leu Cys Ser Pro Gly Cys Phe Ser Leu Phe Arg
        115                 120                 125

Ala Thr Ala Leu Met Glu Asn Ser Val Met Lys Arg Tyr Thr Met Ile
130                 135                 140

Ser Ser Glu Ala Met Lys Met Val Gln Tyr Asp Gln Gly Glu Asp Arg
145                 150                 155                 160

Trp Leu Cys Thr Leu Leu Leu Lys Ala Gly Phe Arg Val Glu Tyr Cys
                165                 170                 175

Gly Ala Ser Asp Gly Tyr Thr His Ala Pro Glu Ser Phe Asn Glu Phe
            180                 185                 190

Tyr Asn Gln Arg Arg Arg Trp Ile Ala Leu Met Asp Asp Asn Val Met
        195                 200                 205

Lys Lys Tyr Thr Thr Arg Ser Asp Glu Ala Arg His Tyr Val Gln Tyr
    210                 215                 220

Asp Gln Gly Glu Asp Arg Trp Leu Cys Thr Leu Leu Leu Gln Arg Gly
225                 230                 235                 240

Tyr Arg Val Glu Tyr Ser Ala Ala Ser Asp Ala Tyr Thr His Ala Pro
                245                 250                 255

Glu Gly Phe Asn Glu Phe Tyr Asn Gln Arg Arg Arg Trp Val
            260                 265                 270
```

<210> SEQ ID NO 3
<211> LENGTH: 28
<212> TYPE: PRT
<213> ORGANISM: Drosophila melanogaster

<400> SEQUENCE: 3

```
Ala Ile Gly His Trp Leu Gln Lys Ala Thr Glu His Val Ile Gly Cys
 1               5                  10                  15

Val Leu Cys Ser Pro Gly Cys Phe Ser Leu Phe Arg
             20                  25
```

```
            20                  25

<210> SEQ ID NO 4
<211> LENGTH: 25
<212> TYPE: PRT
<213> ORGANISM: Drosophila melanogaster

<400> SEQUENCE: 4

Ala Thr Ala Leu Met Glu Asn Ser Val Met Lys Arg Tyr Thr Met Ile
 1               5                  10                  15

Ser Ser Glu Ala Met Lys Met Val Gln
            20                  25

<210> SEQ ID NO 5
<211> LENGTH: 8
<212> TYPE: PRT
<213> ORGANISM: Drosophila melanogaster

<400> SEQUENCE: 5

Gln Gly Glu Asp Arg Trp Leu Cys
 1               5

<210> SEQ ID NO 6
<211> LENGTH: 5
<212> TYPE: PRT
<213> ORGANISM: Drosophila melanogaster

<400> SEQUENCE: 6

Thr Leu Leu Leu Lys
 1               5

<210> SEQ ID NO 7
<211> LENGTH: 32
<212> TYPE: PRT
<213> ORGANISM: Drosophila melanogaster

<400> SEQUENCE: 7

Ala Gly Phe Arg Val Glu Tyr Trp Gly Ala Leu Asp Gly Tyr Thr Gln
 1               5                  10                  15

Ala Pro Glu Ser Phe Asn Glu Phe Tyr Asn Gln Arg Ser Arg Trp Ile
            20                  25                  30

<210> SEQ ID NO 8
<211> LENGTH: 23
<212> TYPE: PRT
<213> ORGANISM: Drosophila melanogaster

<400> SEQUENCE: 8

Ala Leu Met Asp Asp Asn Val Met Lys Lys Tyr Thr Thr Arg Ser Asp
 1               5                  10                  15

Glu Ala Arg His Tyr Val Gln
            20

<210> SEQ ID NO 9
<211> LENGTH: 8
<212> TYPE: PRT
<213> ORGANISM: Drosophila melanogaster

<400> SEQUENCE: 9

Gln Gly Glu Asp Arg Trp Leu Cys
 1               5

<210> SEQ ID NO 10
```

```
<211> LENGTH: 5
<212> TYPE: PRT
<213> ORGANISM: Drosophila melanogaster

<400> SEQUENCE: 10

Thr Leu Leu Leu Gln
 1               5

<210> SEQ ID NO 11
<211> LENGTH: 32
<212> TYPE: PRT
<213> ORGANISM: Drosophila melanogaster

<400> SEQUENCE: 11

Arg Gly Tyr Arg Val Glu Tyr Ser Ala Ala Ser Asp Ala Tyr Thr His
 1               5                  10                  15

Ala Pro Glu Gly Phe Asn Glu Phe Tyr Asn Gln Arg Arg Arg Trp Val
                20                  25                  30

<210> SEQ ID NO 12
<211> LENGTH: 28
<212> TYPE: PRT
<213> ORGANISM: Caenorhabditis elegans

<400> SEQUENCE: 12

Ala Ile Ala His Trp Phe Gln Lys Ala Ala Glu His Val Phe Gly Cys
 1               5                  10                  15

Val Leu Cys Ala Pro Gly Cys Phe Ser Leu Phe Arg
                20                  25

<210> SEQ ID NO 13
<211> LENGTH: 25
<212> TYPE: PRT
<213> ORGANISM: Caenorhabditis elegans

<400> SEQUENCE: 13

Ala Ser Ala Leu Met Asp Asp Asn Ile Met His Lys Tyr Thr Lys Thr
 1               5                  10                  15

Ala Ser Glu Pro Arg His Tyr Val Gln
                20                  25

<210> SEQ ID NO 14
<211> LENGTH: 8
<212> TYPE: PRT
<213> ORGANISM: Caenorhabditis elegans

<400> SEQUENCE: 14

Gln Gly Glu Asp Arg Trp Leu Ser
 1               5

<210> SEQ ID NO 15
<211> LENGTH: 5
<212> TYPE: PRT
<213> ORGANISM: Caenorhabditis elegans

<400> SEQUENCE: 15

Thr Leu Leu Leu Lys
 1               5

<210> SEQ ID NO 16
<211> LENGTH: 63
<212> TYPE: PRT
<213> ORGANISM: Caenorhabditis elegans
```

```
<400> SEQUENCE: 16

Gln Gly Tyr Arg Ile Glu Tyr Ala Ala Ala Ser Asp Ala Glu Thr Tyr
 1               5                  10                  15

Ala Pro Glu Gly Phe Glu Glu Phe Phe Asn Gln Arg Arg Arg Trp Thr
             20                  25                  30

Ala Leu Met Asp Asp Asn Ile Met His Lys Tyr Thr Lys Thr Ala Ser
         35                  40                  45

Glu Pro Arg His Tyr Val Gln Tyr Asp Gln Gly Glu Tyr Val Gln
     50                  55                  60

<210> SEQ ID NO 17
<211> LENGTH: 8
<212> TYPE: PRT
<213> ORGANISM: Caenorhabditis elegans

<400> SEQUENCE: 17

Gln Gly Glu Asp Arg Trp Leu Ser
 1               5

<210> SEQ ID NO 18
<211> LENGTH: 5
<212> TYPE: PRT
<213> ORGANISM: Caenorhabditis elegans

<400> SEQUENCE: 18

Thr Leu Leu Leu Lys
 1               5

<210> SEQ ID NO 19
<211> LENGTH: 32
<212> TYPE: PRT
<213> ORGANISM: Caenorhabditis elegans

<400> SEQUENCE: 19

Gln Gly Tyr Arg Ile Glu Tyr Ala Ala Ala Ser Asp Ala Glu Thr Tyr
 1               5                  10                  15

Ala Pro Glu Gly Phe Glu Glu Phe Phe Asn Gln Arg Arg Arg Trp Thr
             20                  25                  30

<210> SEQ ID NO 20
<211> LENGTH: 35
<212> TYPE: PRT
<213> ORGANISM: Saccharomyces cerevisiae

<400> SEQUENCE: 20

Lys Met Ser Asn Ile Leu Asp Lys Thr Thr Glu Ser Asn Phe Gly Phe
 1               5                  10                  15

Ile Thr Val Leu Pro Gly Ala Phe Ser Ala Tyr Arg Phe Glu Ala Val
             20                  25                  30

Arg Gly Gln
         35

<210> SEQ ID NO 21
<211> LENGTH: 71
<212> TYPE: PRT
<213> ORGANISM: Saccharomyces cerevisiae

<400> SEQUENCE: 21

Leu Gln Lys Tyr Phe Tyr Gly Glu Ile Met Glu Asn Glu Gly Phe His
 1               5                  10                  15

Phe Phe Ser Ser Asn Met Tyr Leu Ala Glu Asp Arg Ile Leu Cys Phe
```

```
                    20                  25                  30

Glu Val Val Thr Lys Lys Asn Cys Asn Trp Ile Leu Lys Tyr Cys Arg
            35                  40                  45

Ser Ser Tyr Ala Ser Thr Asp Val Pro Glu Arg Val Pro Glu Phe Ile
        50                  55                  60

Leu Gln Arg Arg Arg Trp Leu
65                  70

<210> SEQ ID NO 22
<211> LENGTH: 71
<212> TYPE: PRT
<213> ORGANISM: Saccharomyces cerevisiae

<400> SEQUENCE: 22

Leu Gln Lys Tyr Phe Tyr Gly Glu Ile Met Glu Asn Glu Gly Phe His
 1               5                  10                  15

Phe Phe Ser Ser Asn Met Tyr Leu Ala Glu Asp Arg Ile Leu Cys Phe
            20                  25                  30

Glu Val Val Thr Lys Lys Asn Cys Asn Trp Ile Leu Lys Tyr Cys Arg
        35                  40                  45

Ser Ser Tyr Ala Ser Thr Asp Val Pro Glu Arg Val Pro Glu Phe Ile
    50                  55                  60

Leu Gln Arg Arg Arg Trp Leu
65                  70

<210> SEQ ID NO 23
<211> LENGTH: 41
<212> TYPE: PRT
<213> ORGANISM: Saccharomyces cerevisiae

<400> SEQUENCE: 23

Lys Ile Ser Asn Ile Leu Asp Lys Pro Leu Glu Ser Val Phe Gly Tyr
 1               5                  10                  15

Ile Ser Val Leu Pro Gly Ala Leu Ser Ala Tyr Arg Tyr Arg Ala Leu
            20                  25                  30

Lys Asn His Glu Asp Gly Thr Gly Pro
        35                  40

<210> SEQ ID NO 24
<211> LENGTH: 71
<212> TYPE: PRT
<213> ORGANISM: Saccharomyces cerevisiae

<400> SEQUENCE: 24

Leu Arg Ser Tyr Phe Leu Gly Glu Thr Gln Glu Gly Arg Asp His Asp
 1               5                  10                  15

Val Phe Thr Ala Asn Met Tyr Leu Ala Glu Asp Arg Ile Leu Cys Trp
            20                  25                  30

Glu Leu Val Ala Lys Arg Asp Ala Lys Trp Val Leu Lys Tyr Val Lys
        35                  40                  45

Glu Ala Thr Gly Glu Thr Asp Val Pro Glu Asp Val Ser Glu Phe Ile
    50                  55                  60

Ser Gln Arg Arg Arg Trp Leu
65                  70

<210> SEQ ID NO 25
<211> LENGTH: 71
<212> TYPE: PRT
<213> ORGANISM: Saccharomyces cerevisiae
```

```
<400> SEQUENCE: 25

Leu Arg Ser Tyr Phe Leu Gly Glu Thr Gln Glu Gly Arg Asp His Asp
 1               5                  10                  15

Val Phe Thr Ala Asn Met Tyr Leu Ala Glu Asp Arg Ile Leu Cys Trp
                20                  25                  30

Glu Leu Val Ala Lys Arg Asp Ala Lys Trp Val Leu Lys Tyr Val Lys
            35                  40                  45

Glu Ala Thr Gly Glu Thr Asp Val Pro Glu Asp Val Ser Glu Phe Ile
        50                  55                  60

Ser Gln Arg Arg Arg Trp Leu
 65                  70

<210> SEQ ID NO 26
<211> LENGTH: 67
<212> TYPE: PRT
<213> ORGANISM: Saccharomyces cerevisiae

<400> SEQUENCE: 26

Tyr Ile Ser His His Gln Ala Lys Ala Phe Glu Ser Val Phe Gly Ser
 1               5                  10                  15

Val Thr Cys Leu Pro Gly Cys Phe Ser Met Tyr Arg Ile Lys Ser Pro
                20                  25                  30

Lys Gly Ser Asp Gly Tyr Trp Val Pro Val Leu Ala Asn Pro Asp Ile
            35                  40                  45

Val Glu Arg Tyr Ser Asp Asn Val Thr Asn Thr Leu His Lys Lys Asn
        50                  55                  60

Leu Leu Leu
 65

<210> SEQ ID NO 27
<211> LENGTH: 8
<212> TYPE: PRT
<213> ORGANISM: Saccharomyces cerevisiae

<400> SEQUENCE: 27

Leu Gly Glu Asp Arg Phe Leu Ser
 1               5

<210> SEQ ID NO 28
<211> LENGTH: 65
<212> TYPE: PRT
<213> ORGANISM: Saccharomyces cerevisiae

<400> SEQUENCE: 28

Ser Leu Met Leu Lys Thr Phe Pro Lys Arg Lys Gln Val Phe Val Pro
 1               5                  10                  15

Lys Ala Ala Cys Lys Thr Ile Ala Pro Asp Lys Phe Lys Val Leu Leu
                20                  25                  30

Ser Gln Arg Arg Arg Trp Ile Val Leu Ala Asn Pro Asp Ile Val Glu
            35                  40                  45

Arg Tyr Ser Asp Asn Val Thr Asn Thr Leu His Lys Lys Asn Leu Leu
        50                  55                  60

Leu
 65

<210> SEQ ID NO 29
<211> LENGTH: 8
<212> TYPE: PRT
```

<213> ORGANISM: Saccharomyces cerevisiae

<400> SEQUENCE: 29

Leu Gly Glu Asp Arg Phe Leu Ser
 1               5

<210> SEQ ID NO 30
<211> LENGTH: 39
<212> TYPE: PRT
<213> ORGANISM: Saccharomyces cerevisiae

<400> SEQUENCE: 30

Ser Leu Met Leu Lys Thr Phe Pro Lys Arg Lys Gln Val Phe Val Pro
 1               5                  10                  15

Lys Ala Ala Cys Lys Thr Ile Ala Pro Asp Lys Phe Lys Val Leu Leu
                20                  25                  30

Ser Gln Arg Arg Trp Ile
            35

<210> SEQ ID NO 31
<211> LENGTH: 28
<212> TYPE: PRT
<213> ORGANISM: Rhizobium leguminosarum

<400> SEQUENCE: 31

Trp Leu Ala Cys Asn Glu Glu Arg Ala Ala Gln Ala Arg Phe Gly Ala
 1               5                  10                  15

Val Met Cys Cys Cys Gly Pro Cys Ala Met Tyr Arg
                20                  25

<210> SEQ ID NO 32
<211> LENGTH: 5
<212> TYPE: PRT
<213> ORGANISM: Rhizobium leguminosarum

<400> SEQUENCE: 32

Arg Ser Ala Met Leu
 1               5

<210> SEQ ID NO 33
<211> LENGTH: 6
<212> TYPE: PRT
<213> ORGANISM: Rhizobium leguminosarum

<400> SEQUENCE: 33

Ser Leu Leu Asp Gln Tyr
 1               5

<210> SEQ ID NO 34
<211> LENGTH: 9
<212> TYPE: PRT
<213> ORGANISM: Rhizobium leguminosarum

<400> SEQUENCE: 34

Glu Thr Gln Leu Tyr Arg Gly Lys Pro
 1               5

<210> SEQ ID NO 35
<211> LENGTH: 8
<212> TYPE: PRT
<213> ORGANISM: Rhizobium leguminosarum

<400> SEQUENCE: 35

Phe Gly Glu Asp Arg His Leu Thr
 1               5

<210> SEQ ID NO 36
<211> LENGTH: 5
<212> TYPE: PRT
<213> ORGANISM: Rhizobium leguminosarum

<400> SEQUENCE: 36

Ile Leu Met Leu Ser
 1               5

<210> SEQ ID NO 37
<211> LENGTH: 35
<212> TYPE: PRT
<213> ORGANISM: Rhizobium leguminosarum

<400> SEQUENCE: 37

Ala Gly Phe Arg Thr Glu Tyr Val Pro Ser Ala Ile Ala Ala Thr Val
 1               5                  10                  15

Val Pro Asp Thr Met Gly Val Tyr Leu Arg Gln Gln Leu Arg Trp Ala
            20                  25                  30

Ala Met Leu
        35

<210> SEQ ID NO 38
<211> LENGTH: 6
<212> TYPE: PRT
<213> ORGANISM: Rhizobium leguminosarum

<400> SEQUENCE: 38

Ser Leu Leu Asp Gln Tyr
 1               5

<210> SEQ ID NO 39
<211> LENGTH: 9
<212> TYPE: PRT
<213> ORGANISM: Rhizobium leguminosarum

<400> SEQUENCE: 39

Glu Thr Gln Leu Tyr Arg Gly Lys Pro
 1               5

<210> SEQ ID NO 40
<211> LENGTH: 8
<212> TYPE: PRT
<213> ORGANISM: Rhizobium leguminosarum

<400> SEQUENCE: 40

Phe Gly Glu Asp Arg His Leu Thr
 1               5

<210> SEQ ID NO 41
<211> LENGTH: 5
<212> TYPE: PRT
<213> ORGANISM: Rhizobium leguminosarum

<400> SEQUENCE: 41

Ile Leu Met Leu Ser
 1               5

<210> SEQ ID NO 42
<211> LENGTH: 32
<212> TYPE: PRT

-continued

```
<213> ORGANISM: Rhizobium leguminosarum

<400> SEQUENCE: 42

Ala Gly Phe Arg Thr Glu Tyr Val Pro Ser Ala Ile Ala Ala Thr Val
 1               5                  10                  15

Val Pro Asp Thr Met Gly Val Tyr Leu Arg Gln Gln Leu Arg Trp Ala
            20                  25                  30
```